US009550055B2

United States Patent
Cuzydlo

(10) Patent No.: US 9,550,055 B2
(45) Date of Patent: Jan. 24, 2017

(54) RECEIVER WITH VALVES

(71) Applicant: Piramal Critical Care, Inc., Orchard Park, NY (US)

(72) Inventor: Michael Cuzydlo, Orchard Park, NY (US)

(73) Assignee: Piramal Critical Care, Inc., Orchard Park, NY (US)

( * ) Notice: Subject to any disclaimer, the term of this patent is extended or adjusted under 35 U.S.C. 154(b) by 433 days.

(21) Appl. No.: 13/920,038

(22) Filed: Jun. 17, 2013

(65) Prior Publication Data
US 2014/0034163 A1    Feb. 6, 2014

Related U.S. Application Data

(62) Division of application No. 12/813,155, filed on Jun. 10, 2010, now Pat. No. 8,485,235.

(60) Provisional application No. 61/218,696, filed on Jun. 19, 2009.

(51) Int. Cl.
*A61M 39/24* (2006.01)
*A61M 16/18* (2006.01)
*A61M 39/26* (2006.01)

(52) U.S. Cl.
CPC ........... *A61M 39/24* (2013.01); *A61M 16/183* (2013.01); *A61M 39/26* (2013.01); *A61M 2039/2473* (2013.01); *Y10T 137/86196* (2015.04); *Y10T 137/87957* (2015.04)

(58) Field of Classification Search
CPC ................... A61M 39/26; A61M 39/22; Y10T 137/88046; Y10T 137/87973
USPC ......... 141/302, 348–354, 383; 137/628, 637, 137/637.05, 613, 614, 614.19, 614.06, 68.14; 251/149.9
See application file for complete search history.

(56) References Cited

U.S. PATENT DOCUMENTS

| | | | |
|---|---|---|---|
| 2,556,221 A * | 6/1951 | Samiran ........................ | 141/224 |
| 6,539,970 B1 * | 4/2003 | Knowles et al. ............. | 137/238 |
| 6,585,016 B1 * | 7/2003 | Falligant et al. ............. | 141/352 |
| 6,672,327 B1 * | 1/2004 | Krywitsky ................. | 137/68.14 |
| 6,719,003 B2 * | 4/2004 | Schroeder ............. | F16K 15/063 137/234.5 |
| 8,485,235 B2 * | 7/2013 | Cuzydlo ........................ | 141/351 |
| 2005/0011584 A1 * | 1/2005 | Nikolayev et al. ........... | 141/352 |
| 2007/0199616 A1 * | 8/2007 | Chotenovsky ................ | 141/351 |
| 2009/0188582 A1 * | 7/2009 | Hagano et al. ............... | 141/349 |

* cited by examiner

Primary Examiner — Timothy L Maust
Assistant Examiner — Timothy P Kelly
(74) Attorney, Agent, or Firm — Tarolli, Sundheim, Covell & Tummino LLP

(57) ABSTRACT

An apparatus and system for transferring a liquid, such as an anesthetic, from the outlet port of a reservoir to a machine while effectively and conveniently minimizing the release of anesthetic. In one embodiment, the apparatus and system can include a first valve movable between a first position and a second position; a first housing surrounding the first valve; a second valve slidably connected to the first valve and movable between a third position and a fourth position; and a second housing which surrounds the second valve; wherein the apparatus defines a first opening, a second opening, and a receiver passage between the first and second openings. In another embodiment, a movable plunger can be slidably connected to the second valve.

7 Claims, 5 Drawing Sheets

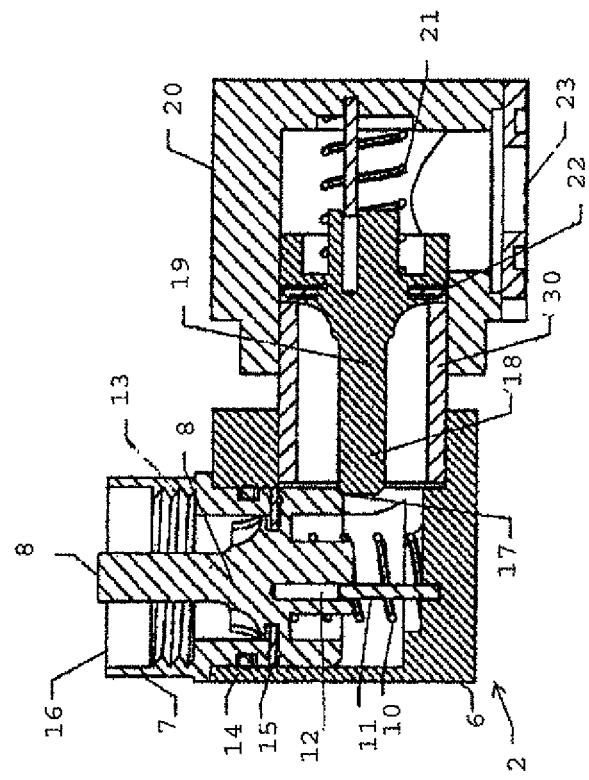
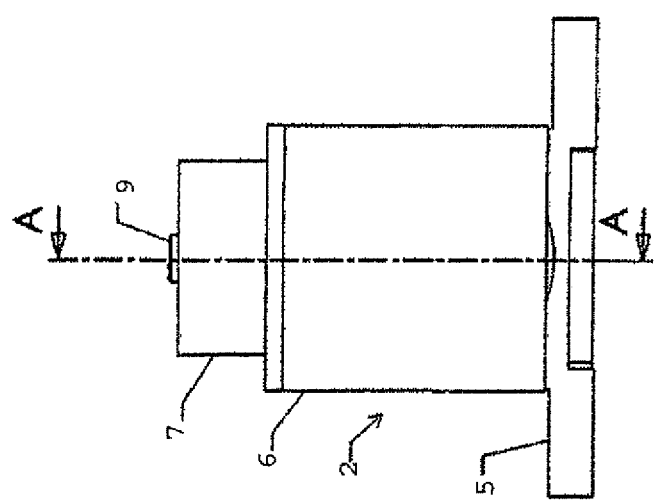
Figure 2B
Figure 2A

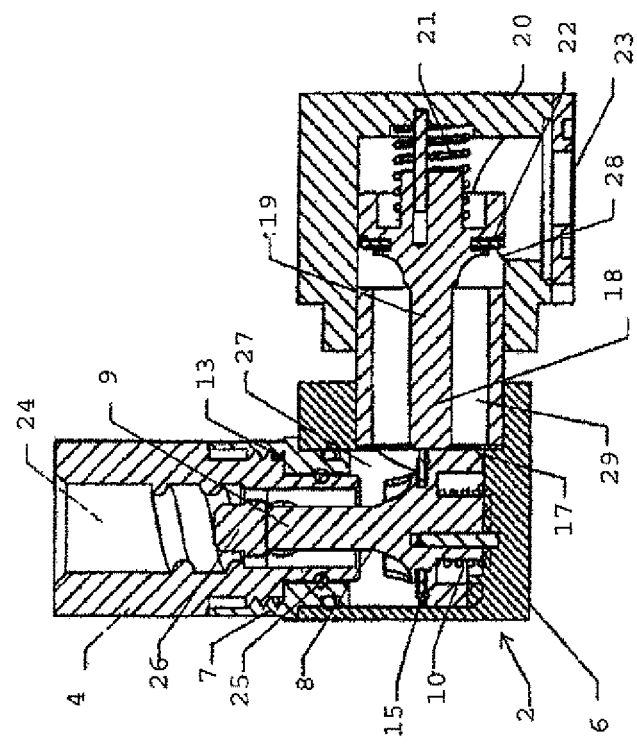
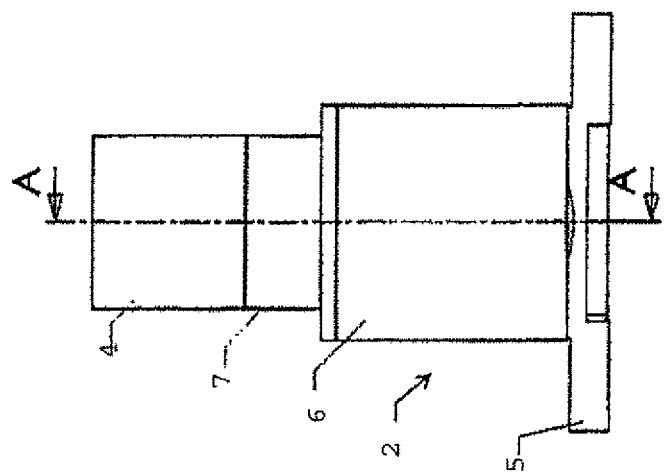
Figure 3B
Figure 3A

US 9,550,055 B2

RECEIVER WITH VALVES

CROSS-REFERENCE TO RELATED APPLICATION

This application is a Divisional of application Ser. No. 12/813,155, filed on Jun. 10, 2010 (now pending), which claims the benefit under 35 U.S. C. §119 (e) of the earlier filing date of U.S. Provisional Application Ser. No. 61/218, 696 filed on Jun. 19, 2009, the contents of which are hereby incorporated by reference.

FIELD OF THE INVENTION

This application discloses an invention which is related, generally and in various embodiments, to a device for supplying a liquid to a machine, such as a vaporizer.

BACKGROUND OF THE INVENTION

Liquid anesthetics are often packaged in glass bottles and shipped to a location where they may be used to anesthetize a patient undergoing a medical or dental procedure. Such anesthetics may also be used to induce analgesia in a patient undergoing a medical or dental procedure. In order to administer the anesthetic, the contents of the glass bottle are placed in a vaporizer. The vaporizer can vaporize the anesthetic and provide the vaporized anesthetic in a desired amount to the patient.

Inhalable anesthetics are typically volatile substances with relatively low boiling points and high vapor pressure. Preferably, there is little or no release of anesthetic to the atmosphere during handing. The opening of a bottle containing vaporizer can be covered by a closing mechanism having an outlet port. To transfer the liquid anesthetic to a vaporizer, however, the outlet port must be opened. Since it is unwise to expose medical personnel performing a procedure to an anesthetic, and since anesthetics are expensive, devices have been developed to minimize the release of anesthetic from a bottle to the environment surrounding a vaporizer. These devices, however, have failed to conveniently and effectively minimize the release of anesthetic.

SUMMARY OF THE INVENTION

This application discloses an apparatus and system for transferring a liquid, such as an anesthetic, from the outlet port of a reservoir to a machine while effectively and conveniently minimizing the release of anesthetic. In one embodiment, the apparatus and system can include a first valve movable between a first position and a second position; a first housing surrounding the first valve; a second valve slidably connected to the first valve and movable between a third position and a fourth position; and a second housing which surrounds the second valve; wherein the apparatus defines a first opening, a second opening, and a receiver passage between the first and second openings. In another embodiment, the apparatus can include a first valve movable between a first position and a second position; a first housing which surrounds the first valve; a plunger member surrounded by the first housing, wherein the plunger member is movable between a third position and a fourth position; a second valve slidably connected to the plunger member, wherein the second valve is movable between a fifth position and a sixth position; and a second housing which surrounds the second valve; wherein the apparatus defines a first opening, a second opening, and a passageway between the first and second openings.

BRIEF DESCRIPTION OF THE DRAWINGS

FIG. 2A illustrates a receiver apparatus in the closed position according to various embodiments.
FIG. 2B shows a cross section of FIG. 2A.
FIG. 3A illustrates the receiver apparatus in the open position according to various embodiments.
FIG. 3B shows a cross section of FIG. 3A.

DETAILED DESCRIPTION OF THE INVENTION

The accompanying drawings are intended to provide further understanding of the invention and are incorporated in and constitute a part of the description of the invention. The drawings illustrate various embodiments of the invention and together with the description illustrate principles of the invention.

The drawings should not be taken as implying any necessary limitation on the essential scope of invention. The drawings are given by way of non-limitative example to explain the nature of the invention.

For a more complete understanding of the instant invention reference is now made to the following description taken in conjunction with accompanying drawings.

The various features of novelty which characterize the invention are pointed out specifically in the claims which are a part of this description. For a better understanding of the invention, reference should be made to the drawings and descriptive matter in which there are illustrated and described preferred embodiments of invention.

Figure 1:
FIG. 1 illustrates various embodiments of a system for the flow of liquid.

Referring now to the drawings, wherein like numerals designate identical or corresponding parts throughout the referred views, FIG. 1 shows various embodiments of a system for the flow of liquid. Specifically, FIG. 1 shows the general flow of liquid from a reservoir 1 to the receiver apparatus 2 to a machine 3. The reservoir 1 can be a glass bottle or any other container capable of containing a liquid, such as a liquid anesthetic. At its opening, the reservoir 1 can include an outlet port 4 (see FIGS. 3A and 3B) to threadedly connect to the receiver apparatus 2. As will be described below, the receiver apparatus 2 can include a valve system through which the liquid must travel to reach the machine 3. In this embodiment, the machine 3 is a vaporizer that dispenses anesthetic to a person undergoing a medical procedure.

FIG. 2A shows various embodiments of a receiver apparatus 2, where the receiver apparatus 2 is in the closed position. The receiver apparatus 2 is supported by a base 5. Above a first housing 6 is a mating collar 7 for receiving a reservoir outlet port 4. The first housing 6 and mating collar 7 surround a first valve 8, the stem 9 of which is also visible in FIG. 2A.

FIG. 2B shows a cross section of FIG. 2A at cross axis "A." The first valve 8 can be movable between a first position and a second position. A first valve biasing member 10, such as a spring, can connect to the first valve 8 and the first housing 6, and can bias the movement between the first and second position. The movement of the first valve 8 between the first position and the second position can be guided by a guide pin 11 connected to the first housing 6 and a guide pin bore 12 in the first valve 8. The mating collar 7 defines a threading 13 for receiving a reservoir outlet port 4. A sealing member 14, such as an o-ring, provides a seal between the mating collar 7 and the first housing 6. A first valve sealing member 15, such as an o-ring, can be in contact with the first valve 8 and can prevent the flow of liquid entering a first opening 16 of the receiver apparatus 2. The first valve 8 can further include a first valve cam surface 17 adjacent to a stem 18 of a second valve 19.

FIG. 2B further shows a housing connector member 30 connector member that can connect the first housing 6 and a second housing 20. The housing connector member 30 and the second housing 20 can surround the second valve 19. The second valve 19 can be movable between a first position and a second position. A second valve biasing member 21, such as a spring, can connect to the second valve 19 and the second housing 20, and can bias the second valve's 19 movement between its first and second positions. The movement of the second valve 19 between its first and second positions can be guided in a manner similar to the guide pin 11 and guide pin bore 12 arrangement described with regard to the first valve 8. A second valve sealing member 22, such as an o-ring, can be in contact with the second valve 19 and can prevent liquid in the receiver apparatus 2 from flowing out a second opening 23 of the receiver apparatus 2.

FIG. 3A shows various embodiments of the receiver apparatus 2, where the receiver apparatus 2 has received a reservoir outlet port 4 and is in the open position.

FIG. 3B shows a cross section of the receiver apparatus 2 of FIG. 3A at cross axis "A." The reservoir outlet port 4 has a reservoir outlet passage through which liquid can flow to the receiver apparatus 2. The reservoir outlet port 4 can engage the mating collar 7 by threading 13. An outlet port sealing member 25, such as an o-ring, can provide a seal between the outlet port 4 and the receiver apparatus 2. The reservoir outlet port 4 can further include a plug member 26. When the reservoir outlet port 4 engages the mating collar 7, the plug member 26 can press the stem 9 of the first valve 8 and overcome the first valve biasing member 10, thereby moving the first valve 8 to its second position and opening a first valve passage 27.

The second valve 19 can be slidably connected to the first valve 8. When the first valve 8 begins to move to the second position, the first valve cam surface 17 of the first valve 8 can push the stem 18 of the second valve 19, thereby overcoming the second valve biasing member 21, moving the second valve 19 to its second position, and opening a second valve passage 28. When opened, the first 27 and second 28 valve passages combine to create a receiver passage 29 through which liquid from the reservoir 1 and the first opening 16 can flow to the second opening 23 and, ultimately, to the machine 3.

Figures 4A, 4B:
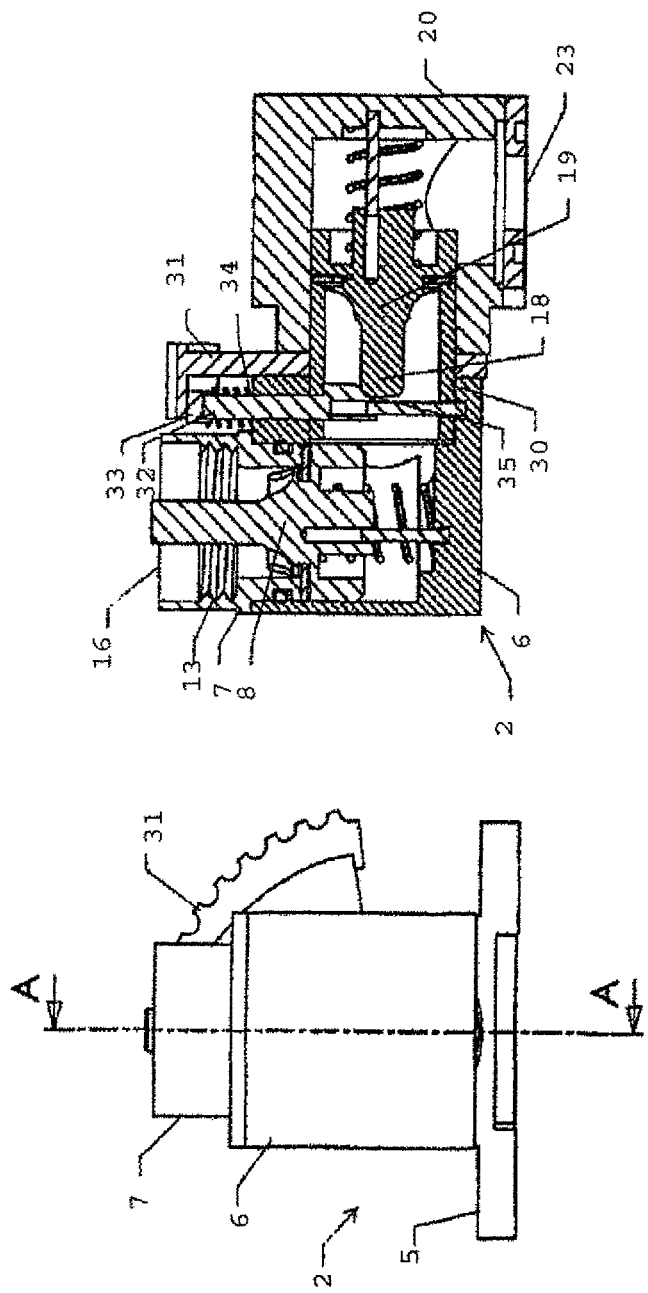
FIG. 4A illustrates the receiver apparatus in the closed position according to other embodiments.
FIG. 4B shows a cross section of FIG. 4A.

FIG. 4A shows various alternative embodiments of the receiver apparatus 2, where the receiver apparatus 2 is in the closed position. Similar to FIG. 2A, the figure shows a mating collar 7, a first housing 6, and a base 5. But by contrast, FIG. 4A also includes an activation member 31 for opening and closing the second valve 19.

FIG. 4B shows a cross section of the receiver apparatus 2 of FIG. 4A at cross axis "A." The figure is similar to FIG. 2B in several respects. Among other similarities, the receiver apparatus 2 of FIG. 4B shows a first valve 8 movable between a first and second position and surrounded by a first housing 6, a second valve 19 movable between a first and second position and surrounded by a second housing 20 and a housing connector member 30, and first 15 and second 22 valve sealing members to help prevent the flow of liquid when the receiver apparatus 2 is in the closed position. Also similar, the mating collar 7 is connected to the first housing 6 and defines a threading 13 for receiving a reservoir outlet port 4, and the receiver apparatus 2 includes a first opening 16 and a second opening 23.

But by contrast, the receiver apparatus 2 of FIG. 4B includes the activation member 31 connected to a plunger member 32. The activation member 31 can be any device connected to or part of a plunger member 32 for opening and closing the second valve 19. In this figure, the activation member 31 is a cam that is positioned between the first housing 6 and the second housing 20. The activation member 31 may rotate about the housing connector member 30 and can move between a first position and a second position. The plunger member 32 and its plunger cap 33 can also be moveable between a first and second position and can be surrounded by the first housing 6. A plunger biasing member 34, such as a spring, can connect to the plunger member 32 and the first housing 6, and can bias the movement of the plunger member 32 between its first and second positions. The plunger member 32 can also include a plunger cam surface 35 adjacent to the stem 18 of the second valve 19.

Figure 5B:
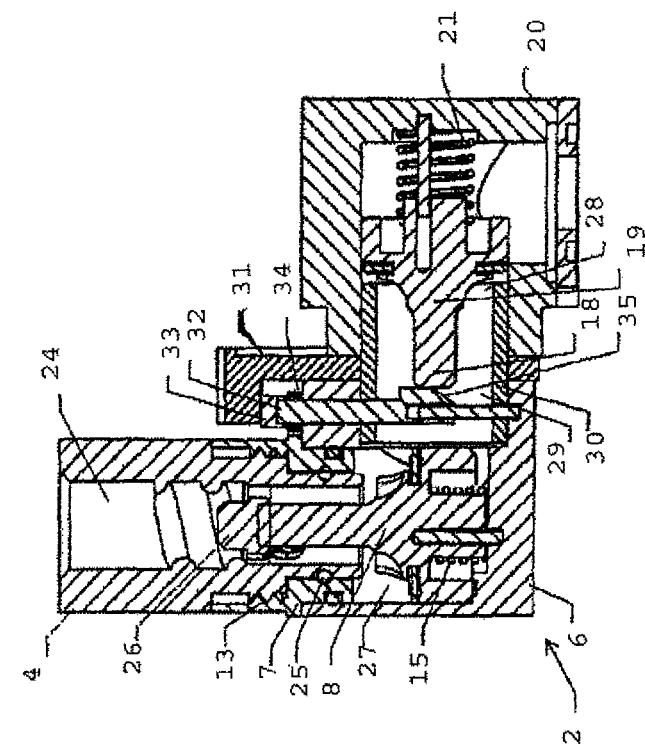
FIG. 5B shows a cross section of FIG. 5A.
Figure 5A:
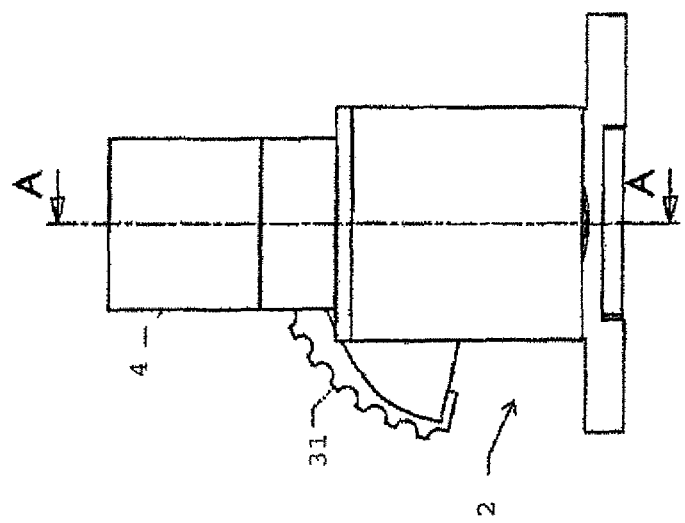
FIG. 5A illustrates the receiver apparatus in the open position according to other embodiments.

FIG. 5A shows various alternative embodiments of the receiver apparatus 2, where the receiver apparatus 2 of FIG. 4A has received a reservoir outlet port 4 and is in the open position.

FIG. 5B shows a cross section of the receiver apparatus 2 of FIG. 5A at cross axis "A." Similar to FIG. 3B, this figure shows, among other things, the reservoir outlet port 4, the reservoir outlet passage 24, the reservoir sealing member 25, and the threading 13 by which the reservoir outlet port 26 can engage the mating collar 7. Also similar to FIG. 3B, the reservoir outlet port 4 can include a plug member 26 such that, when the reservoir outlet port 4 engages the mating collar 7, the plug member 26 can move the first valve 8 to its second position and thereby open the first valve passage 27.

But by contrast, the second valve 19 of FIG. 5B is slidably connected to the plunger member 32, not the first valve 8. Thus, when the reservoir outlet port 4 engages the mating collar 7, the first valve passage 27 may be open while the second valve passage 28 remains closed. To open the second valve passage 28, the activation member 31 can be moved in any suitable manner such that the activation member 31 pushes the plunger member 32 and overcomes the plunger biasing member 34, thereby moving the plunger member 32 to its second position. In FIG. 5B, the activation member 31 is a cam that is positioned between the first housing 6 and the second housing 20, and when the activation member 31 is rotated about the housing connector member 30 from its position in FIG. 4A to its position in FIG. 5A, the housing connector member 30 pushes down the plunger cap 33 and the plunger member 32.

When the plunger member 32 begins to move to its second position, the plunger cam surface 35 of the plunger member 32 can push the stem 18 of the second valve 19 and overcome the second valve biasing member 21, thereby moving the second valve 19 to its second position and opening the second valve passage 28. As shown in FIGS. 4B and 5B, a direction of movement of the plunger member between its first and second position is perpendicular to a direction of movement of the second valve between its first and second position. As in the receiver apparatus 2 of FIG. 3B, when the first 27 and second 28 valve passages are opened they combine to create a receiver passage 29 through which liquid from the reservoir 1 and the first opening 16 can flow to the second opening 23 and, ultimately, to the machine 3.

The various embodiments of FIGS. 4A-5B can provide additional safety to users by opening the first 27 and second 28 valve passages in separate stages. For example, if the receiver apparatus 2 was connected to the reservoir outlet port 4 but not the machine 3, liquid would not automatically flow through the receiver passage 29, but would require the additional movement, manual or otherwise, of the activation member.

It is to be understood that the descriptions of the present invention have been simplified to illustrate characteristics that are relevant for a clear understanding of the present invention. Those of ordinary skill in the art may recognize that other elements or steps are desirable or required in implementing the present invention. However, because such elements or steps are well known in the art, and because they do not facilitate a better understanding of the present invention, a discussion of such elements or steps is not provided herein. The disclosure herein is directed to all such variations and modifications to such elements and methods known to those skilled in the art.

It is to be understood that the invention may assume various alternative orientations and step sequences, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. An anesthetic vaporizer apparatus, comprising:
   a first valve movable between a first position and a second position, a first valve biasing member connected to the first valve, and a first sealing member in contact with the first valve;
   a first housing which surrounds the first valve;
   a plunger member surrounded by the first housing, wherein the plunger member is movable between a third position and a fourth position, a plunger biasing member connected to the plunger member;
   a second valve slidably connected to the plunger member, wherein the second valve is movable between a fifth position and a sixth position, a second valve biasing member connected to the second valve, and a second sealing member in contact with the second valve;
   a second housing which surrounds the second valve; and
   wherein a direction of movement of the plunger member between the third and fourth positions is perpendicular to a direction of movement of the second valve between the fifth and sixth positions;
   wherein the apparatus defines a first opening, a second opening, and a passageway between the first and second openings.

2. The anesthetic vaporizer apparatus of claim 1, wherein:
   the first biasing member is further connected to the first housing; and
   the second biasing member is further connected to the second housing.

3. The anesthetic vaporizer apparatus of claim 1, wherein at least one of the following is a spring:
   the first biasing member;
   the second biasing member; and
   the third biasing member.

4. The anesthetic vaporizer apparatus of claim 1, wherein at least one of the following is an o-ring:
   the first sealing member; and
   the second sealing member.

5. The anesthetic vaporizer apparatus of claim 1, further comprising a housing connector member connected to the first housing and the second housing.

6. The anesthetic vaporizer apparatus of claim 1, wherein an activation member is connected to the plunger member.

7. The anesthetic vaporizer apparatus of claim 6, wherein the activation member is positioned between the first housing and the second housing.

* * * * *